(12) United States Patent
Huang et al.

(10) Patent No.: US 7,825,245 B2
(45) Date of Patent: Nov. 2, 2010

(54) SUBSTITUTED 4-ANILINOQUINAZOLINES AND THEIR USE IN TUMOR TREATMENT

(75) Inventors: Wenlin Huang, Libai Tower 17D, Dongfeng Plaza, Guangzhou City, Guangdong Province 510000 (CN); Xiaohong Zhou, Guangzhou (CN)

(73) Assignees: Wenlin Huang, Guangzhou (CN); Xiahong Zhou, Guangzhou (CN)

( * ) Notice: Subject to any disclaimer, the term of this patent is extended or adjusted under 35 U.S.C. 154(b) by 0 days.

(21) Appl. No.: 11/939,265

(22) Filed: Nov. 13, 2007

(65) Prior Publication Data

US 2008/0167328 A1    Jul. 10, 2008

Related U.S. Application Data

(63) Continuation-in-part of application No. PCT/CN2005/000660, filed on May 12, 2005.

(51) Int. Cl.
*C07D 239/72* (2006.01)
(52) U.S. Cl. .................................. 544/293; 546/199
(58) Field of Classification Search .................. 544/293; 546/199
See application file for complete search history.

(56) References Cited

U.S. PATENT DOCUMENTS 5,770,599 A * 6/1998 Gibson .................... 514/228.2

FOREIGN PATENT DOCUMENTS

| CN | 1542004 A | 11/2004 |
|----|-----------|---------|
| CN | 1231662 C | 12/2004 |
| CN | 1211239 C | 7/2005 |
| CN | 1211240 C | 7/2005 |
| EP | 0635498 B1 | 4/2001 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*

* cited by examiner

*Primary Examiner*—James O Wilson
*Assistant Examiner*—Douglas M Willis
(74) *Attorney, Agent, or Firm*—Occhiuti Rohlicek & Tsao LLP (57) ABSTRACT

The present invention relates to quinazoline derivatives of formula I:

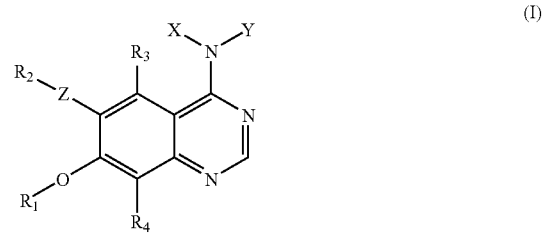

wherein X, Y, Z, $R_1$, $R_2$, $R_3$, and $R_4$ are as defined herein. The invention also relates to a method of preparing these compounds, and use of these compounds for inhibiting tumor growth.

4 Claims, 2 Drawing Sheets

SUBSTITUTED 4-ANILINOQUINAZOLINES AND THEIR USE IN TUMOR TREATMENT

CROSS REFERENCE

This application is a continuation-in-part of PCT Application No. PCT/CN2005/000660, filed on May 12, 2005. The contents of the international application are incorporated by reference.

BACKGROUND

Traditional cancer-treating methods, including radiotherapy, chemotherapy and the electrotherapy for some local solid tumors, have considerable curative effect. However, they also have significant toxic side effect and cause severe pain for patients during the course of treatment.

Most tumors are solid tumors. Their generation, development, recurrence, and transfer all depend on the angiogenesis of tumors, which is an absolutely necessary condition for the growth and transfer of solid tumors. The starvation therapy, which is to inhibit tumor angiogenesis and block the supply of blood for tumor tissues, is considered as one of the most perspective new methods for treating the solid tumor.

The normal construction of tissues and the maintenance of their functions depend on a multistep cell membrane signal transduction from the cell environment to nucleolus in order to transcript and regulate genes. Cancer is an abnormal cell activity caused by a maladjusted signal transduction pathway, for instance, changes in cell growth, survival and functionality and the loss of capability of differentiation. Tumors' growth relies on their autoecious competence in hosts and the angiogenesis to use the nutrition and oxygen of hosts. The development of solid tumors relies on a tumor-generated growth factor, which activates the signal response of endotheliocyte in hosts and extends the tumor blood vessel systems from the existing blood vessels (angiogenesis). The formation rate of adult blood vessels is rather slow and only the endometrium has normal activity of proliferation. The approach of targeted block of angiogenesis is an effective treatment for the pathologic angiogenesis in tumor tissues.

VEGF (Vascular Endothelial Growth Factor), closely relating to the development of solid tumors, is a vascular growth factor in the formation of tumor blood vessels and plays a role in hormonal regulation of the differentiation of endotheliocytes. According to prior research results, many diseases including malignant tumors are related to angiogenesis (Fan, et al, 1995, Trends Pharmacol. Sci. 16, 57-66; Folkman, 1995, Nature Medicine1, 27-31). The change of vascular permeability is thought to play a certain role in both normal and pathologic physiological courses (Cullinan-Bove, et al, 1993, Endocrinology 133, 829-837; Senger, et al, 1993, Cancer and Metastasis Reviews. 12, 303-324). VEGF is an important stimulating factor for the normal and pathological formation of blood vessel and the change of vascular permeability (Jakeman, et al, 1993, Endocrinology 133, 848-859; Kolch, et al, 1995, Breast Cancer Research and Treatment, 36, 139-155; Connolly, et al, 1989, J. Biol. Chem. 264, 20017-20024). The antagonistic action caused by sequestration of VEGF by antibody can inhibit tumor growth (Kim, 1993, Nature 362, 841-844).

The increase in expression of VEGF is the result of stimulation by multiple factors, including the activation of oncogenes and hypoxemia, which can be caused in solid tumors because of the improper perfusion of tumor patients. Besides promoting the angiogenesis, VEGF can also improve the permeability of vascular walls, speed up the exchange of nutrition and metabolite between the tumor and contiguous tissues and reduce the natural barrier of vascular walls to make possible the remote transfer of tumor.

VEGF, via binding to tyrosine kinases (TKs), activates the corresponding signal transduction pathway and stimulate the formation and proliferation of new tumor blood vessels. The RTKs (receptor tyrosine kinases) activated by the combination of VEGF and its receptor play a vital role in the transmembrane signal transduction pathway and thus influence the growth and transfer of tumor. These transmembrane molecules are characterized in that they consist of the extracellular ligand-binding domain linked with the intracellular TKs region through segments in the plasma membrane. The combination of ligand and receptor stimulates the activity of receptor-related TKs and causes the phosphorylation of the tyrosine residues in the receptor and other molecules. The changes of the tyrosine phosphorylation induce a signal cascade and produce numerous cell responses. So far, at least 19 different RTK sub-families have been identified according to the homology of amino acid sequence, one of which contains the TK receptor Flt or Flt1 similar to fms, the receptor KDR (also called Flk-1) with kinase insertion domains and another TK receptor Flt4 similar to fms. It has been proved that two of the correlative RTKs, Flt and KDR can combine with VEGF with high affinity (De Vries, et al, 1992, Science 255, 989-991; Terman, et al, 1992, Boichem. Biophys. Res. Comm., 1992, 187, 1579-1586). The combination of VEGF and the receptor expressed in heterogeneous cells correlates to the tyrosine phosphorylation level of cell proteins and changes of calcium current.

The above discussed research has proved that VEGF is a specific, direct key positive regulator of vascular endothelial cells in the course of angiogenesis of solid tumors. The KDR/Flk-1 pathway between VEGF and its receptor has become one of the main targets of anti-tumor blood vessel therapy. The inhibition of the activity of TKs is an important means to block tumor angiogenesis.

SUMMARY OF THE INVENTION

The present invention relates to a quinazoline compound of formula (I):

wherein X is H, or $C_{1-4}$ alkyl, preferably H or methyl, and most preferably H;

Y is substituted phenyl in which n is 1, 2, 3 or 4; and $R_5$, being identical to or different from each other, is H, methyl, trifluoromethyl, nitro, cyano, $C_{2-4}$ alkyl, $C_{2-4}$ alkoxyl, N—($C_{2-4}$) alkylamine, enzyme, hydroxyl, N,N-3N($C_{1-4}$) alkylamine, $C_{1-4}$ alkylthio, $C_{1-4}$ alkyl sulfonyl, preferably $C_{2-4}$ alkyl, nitro, cyano, $C_{2-4}$ alkoxyl, N—($C_{2-4}$) alkylamine, hydroxyl or $C_{1-4}$ alkylthio, most preferably $C_{2-4}$ alkyl, $C_{2-4}$ alkoxyl, or N—($C_{2-4}$) alkylamine;

Z is —CO$_2$—, O, S, NH, preferably —CO$_2$—, O, or S, and most preferably —CO$_2$—.

O, S or NH, preferably

O or S, and most preferably $R_1$ is $C_{1-4}$ alkyl; and most preferably methyl;

$R_2$ is $C_{1-5}$ alkyl-$R_6$, $C_{2-6}$ alkenyl-$R_6$ or $C_{2-6}$ alkynyl-$R_6$; the alkyl, alkenyl, and alkynyl is optionally substituted with one or more alkynyl, enzymes, or amidos; and $R_6$ is 4-piperidino optionally substituted with one or more alkynyl, enzymes, or amidos; preferably $R_2$ is $C_{1-5}$ alkyl-$R_6$ or $C_{2-6}$ alkenyl-$R_6$, $R_2$ is most preferably $C_{1-5}$ alkyl-$R_6$; $R_6$ is preferably 4-piperidino, and most preferably 4-ethyl-1-piperidino; and $R_3$ and $R_4$, independently, are H, $C_{1-4}$ alkyl, $C_{2-6}$ alkenyl, $C_{2-6}$ alkynyl, cycloalkyl or heteroocycloalkyl, preferably H, $C_{1-4}$ alkyl (e.g., methyl) or $C_{2-6}$ alkenyl; $R_3$ is preferably $C_{1-4}$ alkyl, and most preferably methyl; $R_4$ is preferably hydrogen.

The term "alkyl" refers to a saturated, linear or branched hydrocarbon moiety, such as —CH$_3$, —CH(CH$_3$)$_2$, or —CH$_2$—. The term "alkenyl" refers to a linear or branched hydrocarbon moiety that contains at least one double bond, such as —CH=CH—CH$_3$ or —CH=CH—CH$_2$—. The term "alkynyl" refers to a linear or branched hydrocarbon moiety that contains at least one triple bond, such as —C≡C—CH$_3$ or —C≡C—CH$_2$—. The term "cycloalkyl" refers to a $C_3$-$C_8$ saturated, cyclic hydrocarbon moiety, such as cyclohexyl or cyclohexylene. The term "heterocycloalkyl" refers to a $C_1$-$C_8$ saturated, cyclic moiety having at least one ring heteroatom (e.g., N, O, or S), such as 4-tetrahydropyranyl or 4-tetrahydropyranylene. The term "alkoxyl" refers to a radical of —O-alkyl. The term "alkylamino" refers to an alkyl-substituted amino group. The term "alkylthio" refers to a radical of —S-alkyl.

Alkyl, alkenyl, alkynyl, cycloalkyl, and heterocycloalkyl, mentioned herein include both substituted and unsubstituted moieties, unless specified otherwise. Possible substituents on cycloalkyl and heterocycloalkyl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The term "enzyme" refers to an active protein, which, when attached to the substrate, generates effective physiological reactions.

All of the quinazoline compounds described above include the compounds themselves, as well as their salts. The salts, for example, can be formed between a positively charged moiety (e.g., amine) on the compounds and an anion. Suitable anions include, but are not limited to, chloride, bromide, iodide, sulfate, nitrate, phosphate, citrate, methanesulfonate, trifluoroacetate, and acetate.

This invention also relates to a method of preparing the compound of formula (I). The method includes reacting a compound of formula (III) with a compound of formula (IV):

wherein $R_1$ is $C_{1-4}$ alkyl (e.g., methyl);

$R_2$ is $C_{1-5}$ alkyl-$R_6$, $C_{2-6}$ alkenyl-$R_6$ or $C_{2-6}$ alkynyl-$R_6$; the alkyl, alkenyl, and alkynyl is optionally substituted with one or more alkynyl, enzymes, or amidos; and $R_6$ is 4-piperidino optionally substituted with one or more alkynyl, enzymes, or amidos; $R_3$ and $R_4$ are, independently, H, $C_{1-4}$ alkyl (e.g., methyl), $C_{2-6}$ alkenyl, $C_{2-6}$ alkynyl, cycloalkyl, or heterocycloalkyl;

Z is O, NH, or S;

$L^1$ is a leaving group that can be easily substituted by another functional group, examples of a leaving group including halogen, alkoxyl (preferably $C_{1-4}$ alkoxyl), aryloxy, sulfonyloxy, etc. (for instance, bromine, methoxyl, phenoxyl, methyl sulfonyloxy, or benzyl-4-sulfonyloxy);

X is H or $C_{1-4}$ alkyl (e.g., methyl); and

Y is substituted phenyl in which n is 1, 2, 3 or 4; and $R_5$, being identical to or different from each other, is H, methyl, trifluoromethyl, nitro, cyano, $C_{2-4}$ alkyl, $C_{2-4}$ alkoxyl, N—($C_{2-4}$) alkylamine, enzyme, hydroxyl, N,N-3N—($C_{1-4}$) alkylamine, $C_{1-4}$ alkylthio, or $C_{1-4}$ alkyl sulfonyl.

This invention also relates to a method of inhibiting tumor growth, VEGF-induced propagation of human umbilical vein endothelial cells, and the activity of KDR tyrosine kinase, using the compound of formula (I).

Also within the scope of this invention is use quinazoline compound to prepare an antiphlogistics or to prepare a medicament for inhibiting tumor growth, VEGF-induced propagation of human umbilical vein endothelial cells, or activity of KDR tyrosine kinase.

Other features or advantages of the present invention will be apparent from the following detailed description of several embodiments and the figures, and also from the appending claims.

DETAILED DESCRIPTION

The compounds of this invention can be synthesized by the above-described reaction. The reaction may be performed in the presence of acid or base. The acid may be inorganic acid, such as hydrochloric acid, sulfuric acid, hydrobromic acid, phosphoric acid, trichloroacetic acid, citric acid or maleic acid, preferably hydrochloric acid.

The base may be organic amino base, such as pyridine, 2,6-dimethylpyridine, trimethylpyridine, 4-dimethylamino pyridine, triethylamine, morphine, N-codeine or 1,8-diazabi-cyclo(5,4,0)undecene-7, or the carbonate or hydroxide of alkali metals and alkaline earth metals, such as sodium carbonate, potassium carbonate, calcium carbonate, sodium hydroxide or potassium hydroxide. The base may also be the hydride of alkali metals, such as sodium hydride, or the amide of the alkali metals and alkaline earth metals, such as sodium amide or sodium bis(trimethylsilyl)amide, preferably 2,6-dimethyl pyridine.

The reaction may be performed in the presence of an inert solvent or diluent, such as alkyl alcohol or ester (e.g. methanol, ethanol, isopropanol, or ethyl acetate), halogenated hydrocarbon (e.g. dichloromethane, chloroform or carbon tetrachloride), ether (e.g. tetrahydrofuran or 1,4-dioxan), arene (e.g. toluene), nonpolar solvent with dipole moment (e.g. N,N-dimethylformamide, N,N-dimethylacetamide, N-methylpyrrole-2-one or dimethylsulfoxide); and preferably ethyl acetate.

In addition, the reaction may be performed at a temperature of 10-150° C. (particularly 20-80° C.).

The reaction process can produce free base or salt of the compound of the present invention (together with the H-L$^1$ acid, wherein L$^1$ is defined as above). In order to attain free base from salt, one can treat the salt with said base according to conventional methods.

In the above reaction, compounds of formula (III) are used as starting material. These compounds and their salts (wherein L$^1$ is halogen) can be produced by halogenation of a compound of formula (V):

wherein R$_1$ is methyl or C$_{1-4}$ alkyl;

R$_2$ is C$_{1-5}$ alkyl-R$_6$, C$_{2-6}$ alkenyl-R$_6$ or C$_{2-6}$ alkynyl-R$_6$; the alkyl, alkenyl, and alkynyl is optionally substituted with one or more alkynyl, enzymes, or amidos; and R$_6$ is 4-piperidino optionally substituted with one or more alkynyl, enzymes, or amidos;

R$_3$ and R$_4$ are H, C$_{1-4}$ alkyl (e.g., methyl), C$_{2-6}$ alkenyl, C$_{2-6}$ alkynyl, cycloalkyl or heterocycloalkyl; and Z is O, NH, or S.

Examples of suitable halogenating agents include inorganic acid halide, such as thionyl chloride, phosphorus trichloride, phosphorus oxychloride and phosphorus pentachloride. The reaction may be performed in the presence of an inert solvent or diluent (such as halogenated solvents, e.g. dichloromethane, chloroform or carbon tetrachloride, or aromatic hydrocarbon solvents, e.g. benzene and toluene). A certain temperature range (e.g. 10-150° C., particularly 40-100° C.) can be used to perform this reaction.

Compounds of formula (I) and their salts can also be synthesized by other conventional methods. Synthetic chemistry transformations useful in synthesizing these compounds are known in the art and include, for example, those described in EP 0520722, EP 0566226, EP 0602851, EP 0635498, WO 97/22596, WO 97/30035, WO 97/32856 and WO 98/133541.

A further object of the present invention is to provide a method of treating tumor using the above compound.

Compounds of formula (I) act specifically on TKs to inhibit their activity, so as to inhibit the activities of two high affinity receptors of VEGF, thereby regulating the secretion of VEGF. VEGF is the main angiogenesis factor in tumor vascular tissues. The expression of tumor VEGF is closely related to some complications of malignant solid tumors. Preclinical research data shows that obvious antitumor effect has been displayed in experiments on animals with appropriate tolerance dose. The inhibition of secretion of VEGF factor can indirectly bock tumor growth and result in treatment of diseases. Compared with the traditional tumor-treating methods, the present invention has advantages of accurate targeting and insignificant toxic side effects.

It has been proved that RTKs are important intracellular signal transduction regulators. These proteins are composed by the connection of an extracellular ligand binding site to an intracellular TKs site through the transmembrane primitive or to the receptor forming a receptor, polymer and activated RTKs site. The activity of these enzymes catalyzes the V phosphate cluster transferring to the TKs' own tyrosine by ATP and the specialized inhibition related to KDP to impede the VEGF regulatory signal in endotheliocytes. The growth of solid tumors is the result of constant vascular formation.

Angiogenesis is the necessary condition for the growth of all solid tumors and the formation of metastatic tumors. During this course, VEGF plays a key role and is a protein inhibitor of KDR tyrosine kinase. The compounds of formula (I) can be used to inhibit the VEGF-driven vascular formation, thereby inhibiting the tumor growth and subsequently treating tumors.

To treat tumor, one can administer to a subject an effective amount of the compound of formula (I).

As used herein, the term "treating" or "treatment" is defined as the application or administration of a composition including a compound to a subject, who has a disorder (e.g., tumor), a symptom of the disorder, a disease or disorder secondary to the disorder, or a predisposition toward the disorder, with the purpose to cure, alleviate, relieve, remedy, or ameliorate the disorder, the symptom of the disorder, the disease or disorder secondary to the disorder, or the predisposition toward the disorder. "An effective amount" refers to an amount of a compound which confers a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on the types of tumors treated, route of administration, excipient usage, and the possibility of co-usage with other therapeutic treatments.

As used herein, the terms "tumor" refer to cells having the capacity for autonomous growth, i.e., an abnormal state or condition characterized by rapidly proliferating cell growth. Examples of tumors include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, or cancer of unknown primary site.

To practice the method of the present invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the quinazoline compounds, or one or more solubilizing agents, can be utilized as pharmaceutical excipients for delivery of the quinzoline compounds. Examples of other carriers include colloidal silicon dioxide, magnesium stearate, cellulose, sodium lauryl sulfate, and D&C Yellow # 10.

The quinazoline compounds of this invention can be screened for their efficacy in treating tumor by one or more of in vitro and in vivo assays described in the examples provided below. Based on the results, an appropriate dosage range and administration route can also be determined.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLES

The compound of the invention is white powder. It is acidic with a pH of about 6.4, and water soluble.

Example 1

Preparation of Compound I-1

I-1 wherein $R_1$ is methyl, $R_2$ is 4-ethyl-1-piperidino, $R_3$ is methyl, $R_4$ is H, X is H, Y is tolyl, Z is $L^1$ is Br.

The reaction was conducted by adding equal moles of compounds I-2 and I-3 to a solution containing 10 Vol % of 0.05 mol/L ethyl acetate and hydrochloric acid, heating the reaction mixture in a water bath to 70° C. under agitating, filtrating and isolating the resulting precipitate after 30 minutes, and then drying the solid to obtain compound I-1 as a water-soluble white powder, with a pH of 6.4.

Example 2

The compound II-1 of formula (I) was prepared by the synthetic reaction of compound II-2 of formula (II) with compound III-3 of formula (IV), wherein $R_1$ is ethyl, $R_2$ is 4-vinylpiperidino, $R_3$ is H, $R_4$ is methyl, X is methyl, Y is ethylphenyl, Z is and $L^1$ is methoxyl.

The reaction was conducted by adding equal moles of compound II-2 and compound II-3 into a solution containing 8 Vol % of 0.05 mol/L chloroform and 0.2 mol/L sodium hydroxide solution, heating the reaction mixture in a water bath of 50° C. under agitating, filtratring and isolating the precipitate after 30 minutes, and then drying the solid to obtain compound II-1 and as a water-soluble white powder, with a pH of 6.4.

Example 3

The compound III-1 of formula (I) was prepared by the synthetic reaction of compound III-2 of formula (III) with compound III-3 of formula (IV), wherein $R_1$ is methyl, $R_2$ is 4-ethinyl-1-piperidino, $R_3$ is ethyl, $R_4$ is H, X is methyl, Y is tolyl, Z is NH, and $L^1$ is methoxyl.

The reaction was conducted by adding equal moles of compound III-2 and compound III-3 into a solution containing 15 Vol % of 0.05 mol/L isopropyl alcohol and 0.1 mol/L potassium carbonate, heating the reaction mixture in a water bath of 100° C. after mixing and agitating, filtrating and isolating the precipitate after 20 minutes, and then drying the solid to obtain compound III-1 as a water-soluble white powder, with a pH of 6.4.

Example 4

Compound IV-1 of formula (I) was prepared by the synthetic reaction of compound IV-2 of formula (III) with compound IV-3 of formula (IV), wherein $R_1$ is butyl, $R_2$ is 4-vinylpiperidino, $R_3$ is pentynyl, $R_4$ is propenyl, X is propyl, Y is nitro, Z is NH, and $L^1$ is methoxyl.

The reaction was conducted by adding equal moles of compound IV-2 and compound IV-3 into the reaction liquid containing 12 Vol % of 0.08 mol/L toluene and 0.15 mol/L citric acid, heating the reaction mixture in a water bath of 10° C. under agitating, filtrating and isolating the precipitate after 60 minutes, and then drying the solid to obtain compound IV-1 as a water-soluble white powder, with a pH of 6.4.

Example 5

Compound V-1 of formula (I) was prepared by synthetic reaction of compound V-2 of formula (III) with compound V-3 of formula (IV), wherein $R_1$ is propyl, $R_2$ is 4-vinylpiperidino, $R_3$ is H, $R_4$ is methyl, X is methyl, Y is ethylphenyl, Z is S, and $L^1$ is methoxyl.

The reaction was conducted by adding equal moles of compound V-2 and compound V-3 into a solution containing 6 Vol % of 0.05 mol/L tetrahydrofuran and 0.08 mol/L 2,6-dimethyl pyridine, heating the reaction mixture in a water bath of 20° C. under agitating, filtrating and isolating the precipitate after 40 minutes, and then drying the solid to obtain compound V-1 as a water-soluble white powder, with a pH of 6.4.

Example 6

Compound VI-1 of formula (I) was prepared by the synthetic reaction of compound VI-2 of formula (III) with compound VI-3 of formula (IV), wherein $R_1$ is ethyl, $R_2$ is 4-vinylpiperidino, $R_3$ is butenyl, $R_4$ is methyl, X is methyl, Y is ethylphenyl, Z is and $L^1$ is methoxyl.

The reaction was conducted adding equal moles of compound (III) and compound (IV) into a solution containing 5 Vol % of 0.15 mol/L N,N-dimethylacetamide and 0.2 mol/L sodium amide, heating the reaction mixture in a water bath of 60° C. under agitating, filtrating and isolating the precipitate after 30 minutes, then drying the solid to obtain compound VI-2 as a water-soluble white powder, with a pH of 6.4.

Examples 7-13 below study activities of the compound of following formula:

wherein $R_1$ is methyl, $R_2$ is 4-ethyl-1-piperidino, $R_3$ is methyl, $R_4$ is H, X is H, Y is tolyl, and Z is Example 7

Figure 1:
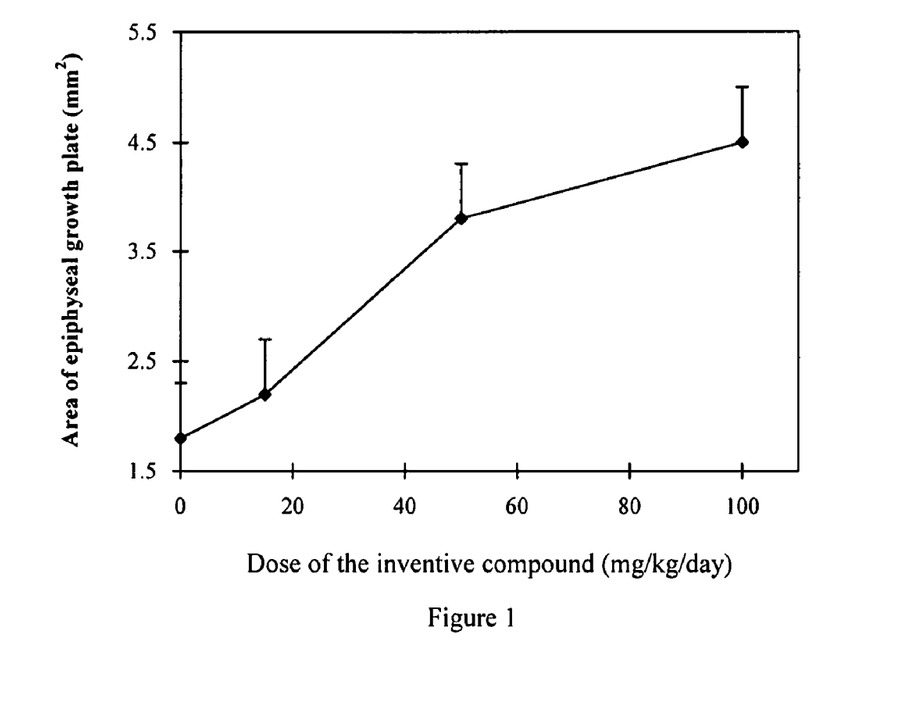
FIG. 1 shows the dose dependence of the joint epiphyseal growth plate of rats on the compound of the invention.

The test compound was administered continuously for 14 days to an Alderley Park young female rat (4-8 weeks old, wostar-derived) by subcutaneous injection at the dose of 0.25 mg/kg/d. The epiphyseal tissue structures of the leg joint of the rat was stained with hematoxylin and eosin. The binding site of the epiphyseal growth plate was measured for dose effect analysis. The results, shown in FIG. 1, indicate that the excess growth of the joint epiphyseal growth plate of rats resulted in growing dose dependence of the cartilage zone. When the dose was increased to 50 or 100 mg/kg/d, the inhibition on VEGF signal by the compound of the invention remained consistent with the in-vivo anti-angiogenesis effect.

Example 8

Figure 2:
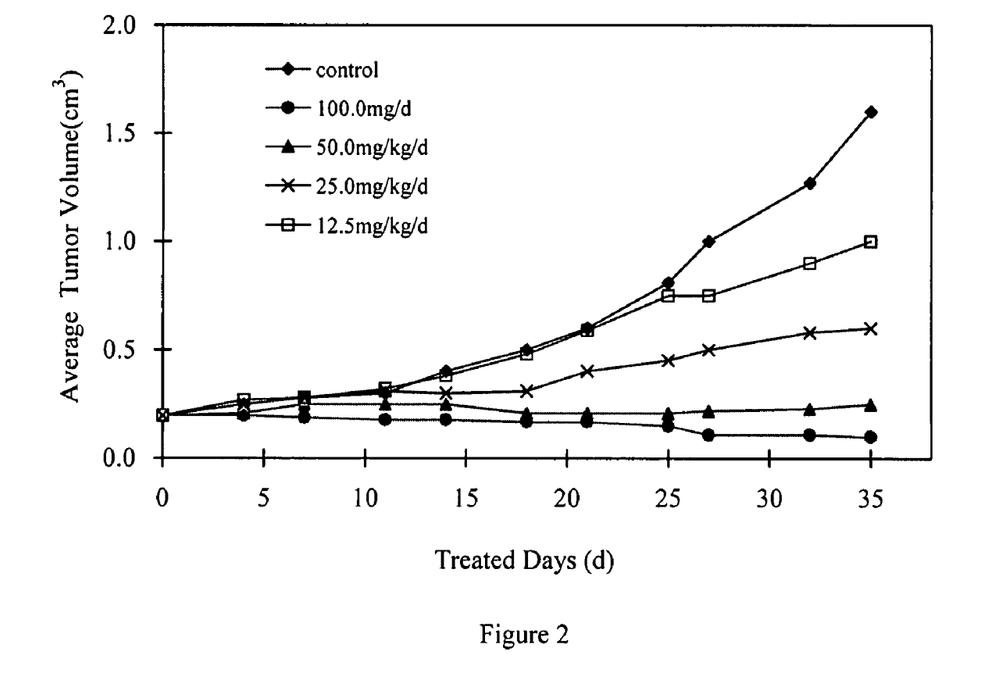
FIG. 2 shows the inhibition of the human prostate tumor planted in nude mouse by the compound of the invention.

PC-3 human prostate tumors were implanted into nude mice (male, 6 weeks old). When the tumor volume reached 0.2 cm³, the mice were randomly divided into 5 groups, including a control group, a dose group of 100 mg/kg/d, a dose group of 50 mg/kg/d, a dose group of 25 mg/kg/d, and a dose group of 12.5 mg/kg/d. The test compound was administered to mice by intratumoral injection continuously for 7 days, and observed for 5 weeks. The results are shown in FIG. 2.

Example 9

Various tumors were inoculated at different body parts of 6-week old, male nude mice. The test compound was orally administered to the mice at different time points after the inoculation. The tumor weights were measured. Results are shown in table 1.

TABLE 1

The inhibition on the human tumors transplanted into nude mice by oral administration of the compound of the present invention

| Transplanted tumors | Tumor place | Oral dose (mg/kg/d) | Experiment times | Inoculation time (d) | Administration times | Tumor-inhibiting ratio (%) | Statistical Difference (P value) |
|---|---|---|---|---|---|---|---|
| MDA-mb-231 | breast | 100 | 1 | 16 | 25 | 99 | <0.001 |
|  |  | 50 | 1 | 16 | 25 | 82 | <0.001 |
|  |  | 25 | 1 | 16 | 25 | 64 | <0.01 |
|  |  | 12.5 | 1 | 16 | 25 | 71 | <0.001 |
| SKOV-3 | ovary | 100 | 1 | 18 | 28 | 100 | <0.001 |
|  |  | 50 | 1 | 18 | 28 | 98 | <0.001 |
|  |  | 25 | 1 | 18 | 28 | 50 | NS |
|  |  | 12.5 | 1 | 18 | 28 | 30 | NS |
| LoVo | colon | 100 | 2 | 5 | 14-17 | 99->100 | <0.001 |
|  |  | 50 | 2 | 5 | 14-17 | 77-81 | <0.01-0.001 |
|  |  | 25 | 2 | 5 | 14-17 | 55-60 | <0.05-0.001 |
|  |  | 12.5 | 2 | 5 | 14-17 | 5-27 | NS |
| A549 | lung | 100 | 1 | 14 | 25 | >100 | <0.001 |
|  |  | 50 | 1 | 14 | 25 | >100 | <0.001 |
|  |  | 25 | 1 | 14 | 25 | 88 | <0.001 |
|  |  | 12.5 | 1 | 14 | 25 | 64 | <0.001 |
|  |  | 12.5 | 1 | 14 | 21-30 | 15-46 | NS-<0.05 |
| A431 | pubes | 100 | 1 | 14 | 21 | >100 | <0.001 |
|  |  | 50 | 2 | 14 | 21-30 | 83->100 | <0.001 |
|  |  | 25 | 2 | 14 | 21-30 | 42-80 | <0.05-<0.001 |
|  |  | 12.5 | 2 | 14 | 21-30 | 15-46 | NS-<0.05 |

NS = not significant

Example 10

Thymidine labeled by ³H (10 μCi/mL) and HUVEC (1×10⁵/mL) were co-cultured to allow integration of thymidine into HUVEC. A series of 10-fold dilutions of the test compound were prepared from an initial concentration of 800 mg/L in sterile distilled water. The dilutions were separately added to into thymidine intergrated HUVEC. The cell division of HUVEC was measured after incubation, and $IC_{50}$ values of the compound for HUVEC were calculated.

As shown in Table 2, the compound significantly and selectively inhibited HUVEC proliferation induced by VEGF, and had no influence on growth of basal endothelial cell even at a concentration 50 times the IC$_{50}$ for the HUVEC proliferation induced by VEGF. Enzyme analysis shows that the compound exhibited different inhibitory activities against KDR, EGFR and FGFR1 (KDR>EGFR>FGFR1), and cellular composition analysis shows that the compound exhibited different inhibitory activities against VEGF, EGF and bFGF (VEGF>EGF>bFGF). Both analyses suggest that the compound have selective inhibitory activities against various growth factors.

TABLE 2

The induction of growth factors' ability and the inhibition on cell division of endothelial cells by the compound of the present invention

| | Mean ± Error | | | |
|---|---|---|---|---|
| | VEGF | EGF | FGF | Basal |
| IC$_{50}$(MM) | 0.06 ± 0.02 | 0.16 ± 0.03 | 0.8 ± 0.06 | >3 |
| Experiment times | 6 | 6 | 5 | 4 |

EGF: Endothelial Growth Factor
FGF: Fibroblast Growth Factor
VEGF: Vascular Endothelial Growth Factor Example 11

$^3$H-containing thymine nucleotide (10 μCi/mL) and tumor cells were co-cultured to allow integration of thymidine into the cells. A series of dilutions of the test compound at a concentration gradient of 10$^{-1}$ starting from an initial concentration of 800 mg/L) were prepared. The solutions were added to the tumor cells integrated with the $^3$H-containing thymine nucleotide. The IC$_{50}$ of the test compound on tumor cells was calculated.

As shown in table 3, the IC$_{50}$ values of the test compound in inhibiting tumor cell growth range from 0.8 to 1.4 mm, 13-230 times the concentration for inhibition of HUVEC division induced by VEGF. These data indicate that the tumor-resisting function of the compound in vivo is mainly to inhibit the endothelial VEGF signal factor, rather than to directly inhibit the growth of tumor cells.

TABLE 3

The effect of the compound of the present invention on the tumor cell division in vivo(n = 3)

| Tumor cell line | origin | mean(±error)IC$_{50}$(MM) |
|---|---|---|
| Calu-6 | lung | 1.30 ± 0.05 |
| MDA-MB-231 | breast | 6.00 ± 1.60 |
| SKOV-3 | ovary | 5.60 ± 0.10 |
| A431 | pubes | 4.80 ± 0.10 |
| A549 | lung | 3.80 ± 0.40 |
| PC-3 | prostate | 3.70 ± 1.40 |
| LoVo | colon | 0.75 ± 0.20 |

Example 12

Colon carcinoma LoVo cells were cultured in the logarithmic phase in a 96-well culture plate for 48 h. The test compound in sterile distilled water at a concentration of 0-100 μg/mL was added to the lovo cells (6 wells for each concentration). RPMI 1640 culture medium without the compound was used in the control group and the RPMI culture medium without the compound and cells was used in the blank control group. After 72 h, 20 μL MTT (5 g/L) was added into each well. After the culture plate was incubated at 37° C. for 4 h, the culture fluid was removed, 150 μL dimethyl sulfoxide (DMSO) was added to each well, and the absorbance (A) was measured at the wavelength of 570 nm.

Figure 3:
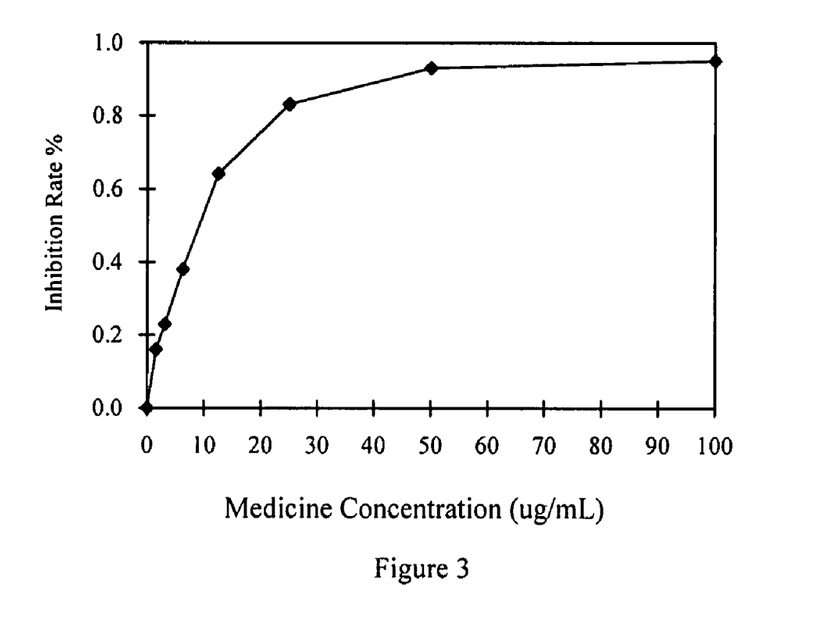
FIG. 3 shows the inhibition of the Lovo growth by the compound of the invention.

FIG. 3 shows that the compound exhibited inhibitory effect on growth of Lovo cells in a dose-dependent manner. The inhibition rate was 50% when the concentration of the compound was 12.5 μg/mL, and over 90% when the concentration was 25 μg/mL.

Example 13

Figure 4:
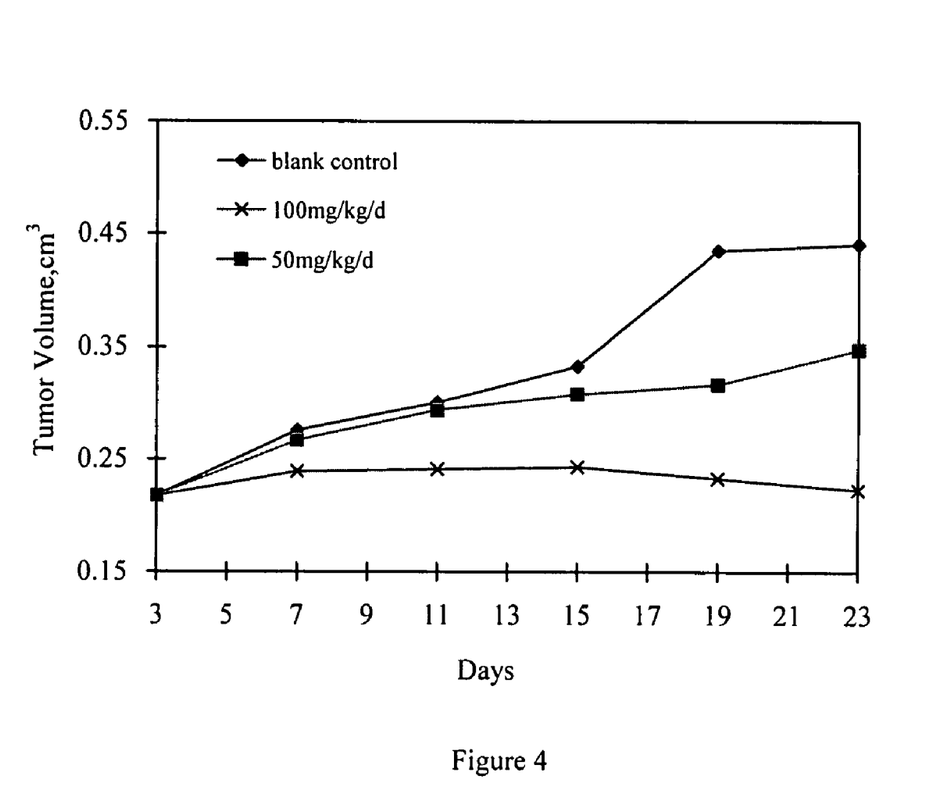
FIG. 4 shows inhibitive effect of the compound of the invention on transplanted tumor in the nude mouse model constructed by use of colon carcinoma cell Lovo.

The test compound was intraperitoneally injected to a nude mice transplanted with colon carcinoma cell LoVo for 30 days at a dose of 100 mg/kg/day or 50 mg/kg/day. For blank control, 0.2 mL of 0.5% DMSO was intraperitoneally injected to nude mice. The mice were then sacrificed. The tumor volumes were measured for calculating T/C ratio, and tumor was weighted for calculating inhibition rate (FIG. 4). The compound selectively inhibited the phosphorylation of KDR tyrosine kinase and blocked the signal transduction of tyrosine kinase, thereby inhibiting the tumor angiogenesis and tumor growth.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the quinazoline compounds of this invention also can be made, screened for their antitumor activities, and used to practice this invention. Thus, other embodiments are also within the claims.

What is claimed is:

1. A quinazoline compound of formula (I):

wherein
X is H or C$_{1-4}$ alkyl;

Y is wherein n is 1; and $R_5$ is, independently, H, trifluoromethyl, nitro, cyano, $C_{1-4}$ alkyl, $C_{2-4}$ alkoxy, N—$(C_{2-4})$ alkylamine, hydroxy, $C_{1-4}$ alkylthio, or $C_{1-4}$ alkyl sulfonyl;

Z is —$CO_2$—, S, or NH;

$R_1$ is $C_{1-4}$ alkyl;

$R_2$ is $C_{1-5}$ alkyl-$R_6$, $C_{2-6}$ alkenyl-$R_6$, or $C_{2-6}$ alkynyl-$R_6$; the alkyl, alkenyl, and alkynyl being optionally substituted with one or more groups selected from alkynyl, and amido; and $R_6$ being piperidin-4-yl optionally substituted with one or more groups selected from alkynyl, and amido; and $R_3$ and $R_4$, independently, are H, $C_{1-4}$ alkyl, $C_{2-6}$ alkenyl, $C_{2-6}$ alkynyl, cycloalkyl or heterocycloalkyl.

2. The compound of claim 1, wherein:

X is H or methyl;

Y is substituted phenyl and $R_5$ is $C_{2-4}$ alkyl, nitro, cyano, $C_{2-4}$ alkoxy, N—$(C_{2-4})$ alkylamine, hydroxy, or $C_{1-4}$ alkylthio;

Z is —$CO_2$— or S;

$R_1$ is methyl;

$R_2$ is $C_{1-5}$ alkyl-$R_6$, $C_{2-6}$ alkenyl-$R_6$ or $C_{2-6}$ alkynyl-$R_6$; the alkyl, alkenyl, and alkynyl being optionally substituted with one or more groups selected from alkynyl, and amido; and $R_6$ being piperidin-4-yl optionally substituted with one or more groups selected from alkynyl, and amido; and $R_3$ and $R_4$, independently, are H, $C_{1-4}$ alkyl, or $C_{2-6}$ alkenyl.

3. A quinazoline compound of formula (I):

wherein

X is H or methyl;

Y is wherein n is 1, and $R_5$ is $C_{2-4}$ alkyl, $C_{2-4}$ alkoxy, or N—$(C_{2-4})$ alkylamine;

Z is —$CO_2$—;

$R_1$ is methyl;

$R_2$ is $C_{1-5}$ alkyl-$R_6$, $R_6$ being piperidin-4-yl optionally substituted with one or more groups selected from alkynyl and amido;

$R_3$ is $C_{1-4}$ alkyl; and $R_4$ is H.

4. A quinazoline compound of formula (I):

wherein

X is H;

Y is 4-tolyl;

Z is —$CO_2$—;

$R_1$ is methyl;

$R_2$ is 4-ethylpiperidinyl;

$R_3$ is methyl; and $R_4$ is H.

* * * * *